United States Patent [19]

McCorkle, Jr.

[11] 4,332,259
[45] Jun. 1, 1982

[54] INTRAVENOUS CHANNEL CARDIAC ELECTRODE AND LEAD ASSEMBLY AND METHOD

[76] Inventor: Charles E. McCorkle, Jr., 1427 E. Bayview Dr., Tempe, Ariz. 85283

[21] Appl. No.: 76,910

[22] Filed: Sep. 19, 1979

[51] Int. Cl.³ .............................................. A61N 1/04
[52] U.S. Cl. ................................ 128/786; 128/419 P
[58] Field of Search ..................... 128/419 P, 784, 785, 128/786

[56] References Cited

U.S. PATENT DOCUMENTS 3,865,118  2/1975  Bures .................................... 128/786
4,057,067  11/1977  Lajos .................................... 128/785

FOREIGN PATENT DOCUMENTS 2605590  8/1977  Fed. Rep. of Germany ... 128/419 P

OTHER PUBLICATIONS

"Medtronics Publication TC68101R", Dec. 1968, pp. 1-21.
Mobin-Uodin et al., "Journal of Thoracic & Cardiovascular Surgery", vol. 54, No. 4, Oct. 1967, pp. 545-548.

Primary Examiner—William E. Kamm
Attorney, Agent, or Firm—Cahill, Sutton & Thomas

[57] ABSTRACT

An intravenous lead assembly for atriolventricular (AV) sequential pacing includes a channel and a separable core lead. The channel lead and the core lead respectively include first and second helical coil conductors through which first and second wire stylets can be inserted. The first and second helical coil conductors are embedded in first and second elongated silicone rubber sleeves, respectively. The silicone rubber sleeve of the channel lead includes an elongated channel. In use, the core lead is passed through the channel of the channel lead either before or after the channel lead is passed through selected veins into a patient's heart. Handles are provided on the proximal ends of the stylets to enable a physician to manipulate the distal ends of the channel lead and core lead. In one embodiment of the invention, the channel terminates in a side port of the channel lead, enabling the physician to guide the top of the core lead out of the side port and into the right ventricle after the distal end of the channel lead has been positioned in the coronary sinus or the right atrial appendage.

16 Claims, 17 Drawing Figures

INTRAVENOUS CHANNEL CARDIAC ELECTRODE AND LEAD ASSEMBLY AND METHOD

BACKGROUND OF THE INVENTION

1. Field of the Invention:

The invention relates to electrodes and leads for conducting electrical signals to and from muscle tissue, and especially to electrodes and leads useful for intravenously conducting such signals to and from endocardial electrodes.

2. Description of the Prior Art:

In the past, various types of endocardial leads and electrodes thereof have been intravenously introduced into different chambers of a patient's heart, including the right ventricle, the atrium, the right atrial appendage, and the coronary sinus. A typical endocardial lead includes a sleeve composed of silicone rubber, which is resistent to deterioration caused by body fluids and does not cause adverse reaction by the patient's body. A helical coil embedded in the silicone rubber sleeve is electrically connected to a distal electrode which is introduced into the heart and a proximal electrode electrically connected to the opposite end of the helical coil conductor to allow electrical connection of the lead to electronic equipment, such as an electronic pacemaker. Typically, a stylet made of thin spring steel wire and having a handle at one end thereof is removeably inserted through the length of the helical coil conductor. Turning of the handle permits a physician to manipulate and control the distal end of the lead as it is intravenously introduced into the heart.

Both unipolar leads (including a single helical coil conductor embedded in a single, silicone rubber sleeve) and bipolar leads (including two helical conductors embedded in a single silicon rubber sleeve) have been utilized. Such intravenous leads are readily available from various manufacturers, including Cardiac Pacemakers, Inc., of St. Paul, Minn., Inter-Medics, Inc., of Freeport, Tex., and Med-Tronic, Inc., of Minneapolis, Minn.

Recently, surgeons have attempted to introduce several leads into the heart of a patient in order to accomplish atrioventricular (AV) sequential pacing, which has been made possible by recently developed AV sequential pulse generators. AV sequential pacing makes it possible for the heart of a patient to achieve maximum cardiac output by causing the upper and lower chambers of the heart to fire in optimum time sequence such that the receiving chamber can receive an optimum amount of blood, which can then be pumped in proper time sequence to the periphery of the body.

Ordinarily, the cephalic veins at the shoulder level or the internal or external jugular veins in the neck of a patient are surgically opened and endocardial leads are introduced through the respective venous openings. The desirability of inserting two endocardial leads to achieve AV sequential pacing has posed a problem to the surgeon, since two (rather than only one) incisions must be made in two veins which have continuity with the right side of the heart in order to pass two endocardial leads intravenously into the heart. The leads must be passed parallel to each other through the accessible veins. This situation can result in dislodgement of a first lead which has been initially inserted into a proper position in the heart. Further, when multiple leads are lodged in different portions of the heart, the leads sometimes rub against each other due to lead flexing caused by beating of the heart. The forces produced as a result of the rubbing sometimes cause dislodging of electrodes attached to the leads. There is presently an unmet need for a reliable system for introducing multiple endocardial leads intravenously into the heart without the surgical complexity that now exists.

Accordingly, it is an object of the invention to provide a system and method of intravenously introducing an endocardial lead into a patient's heart with minimum danger of dislodging an endocardial lead previously introduced and lodged within the patient's heart.

It is another object of the invention to provide a system and method of intravenously introducing an endocardial lead into a patient's heart without the requirement that individual leads be passed through separate incisions into one or more veins of the patient.

It is another object of the invention to provide an endocardial lead system which avoids rubbing between leads due to flexing of the leads caused by beating of the heart in which the leads are lodged.

It has been very difficult to introduce prior endocardial leads into the coronary sinus or to attain the J-shaped curvature necessary to attach an electrode to the right atrial appendage, as is desirable in some instances to attain AV sequential pacing. U.S. Pat. Nos. 3,865,118; 4,057,067; and 4,154,247 disclose endocardial leads designed to make atrial contact. The device disclosed in U.S. Pat. No. 3,865,118 includes a catheter of coaxial design. This device includes spring electrodes connected to both inner and outer conductors for contacting the apex of the ventricle and outer atrium, respectively. This device does not allow the controlling of the positions of the leads, except as to their depth, by the physician. Further, spring electrodes can be a source of clot formation. Further, due to the springing characteristic of electrodes, laceration or perforation of the vena cava can occur. Further, the disclosed device is incapable of contacting optimum muscle tissue locations in the heart to accomplish optimum AV sequential pacing. Further, repositioning of the distal spring electrodes after initial lodging in heart muscle tissue may be dangerous.

It is another object of the invention to provide a multiple lead endocardial lead assembly and method which enables a surgeon to independently control the depth of insertion of a second lead into a second heart chamber, after a first lead has been inserted into a first heart chamber.

It is another object of the invention to provide a multiple lead endocardial lead assembly which does not depend upon springiness of a lead to maintain electrode contact with muscle tissue of the heart.

It is another object of the invention to provide a multiple lead endocardial lead assembly which has no tendency to lacerate heart tissue as a result of continual beating of the heart for a very long period of time.

The device disclosed in U.S. Pat. No. 4,057,067 discloses a single bipolar lead structure having an atrial electrode structure which assumes a J-shaped configuration, enabling the atrial electrode to be hooked onto the atrial appendage at the time the ventricular component and the electrode thereon is firmly engaged against the right ventricular wall. During insertion, a stylet maintains the atrial component in a linear configuration. When the stylet is removed the atrial component springs into the desired J-shaped configuration. This device has the problem that the lengths of the ventricle and atrial tips cannot be adjusted for various sized hearts or anatomical configuration. Further, the ventricle tip can become dislodged when the atrial component is released by withdrawing the stylet. The device is not suitable for stimulating tissue in the coronary sinus.

It is another object of the invention to provide a multiple lead endocardial lead assembly which allows independent adjustment of the depth of one of the leads after another of the leads has been positioned in the heart, and is suitable for insertion of one lead into either the coronary sinus or the atrial appendage and is also suitable for insertion of another lead into the right ventricle.

The device disclosed in U.S. Pat. No. 4,154,247 discloses a bipolar lead including a sheath having an insulating layer which, when heated, by immersing it into boiling water, enables the lead to be formed into a particular configuration. When the lead cools, it "sets" into a new deformable configuration. The device has the shortcoming that it is a bipolar lead having two electrodes disposed along a single lead. It relys on its deformed configuration to maintain spring pressure of the electrode against suitable portions of the ventricle and atrium. This results in unreliable electrical contact to tissue in a beating heart. The device is not suitable for contacting muscle tissue both of the ventricle and the coronary sinus, and provides minimal capacity for manipulation of the electrodes by a physician.

Accordingly, another object of the invention is to provide a multiple lead endocardial assembly and method which overcomes the above shortcomings of prior endocardial leads.

SUMMARY OF THE INVENTION

Briefly described, and in accordance with one embodiment thereof, the invention provides an intravenous composite lead assembly for conducting signals between an electronic floating device such as an atrioventricular pacemaker and various muscles in a patient's heart. The composite lead assembly includes a channel lead and a core lead, each of which has a proximal end for connection to the pacemaker unit and a distal end for connection to electrodes which electrically contact endocardial tissue. The channel lead includes an elongated channel which extends along a substantial portion of the channel lead to a port located at a predetermined distance from the distal end of the channel lead. The port may be either an end port or a side port. The core lead can be slid through the channel of the channel lead and caused to extend from the side port. The channel lead and core lead are each formed of silicone rubber, and each includes at least one flexible conductor surrounded by silicone rubber and extending from the proximal end of the lead to an electrode located at or near the distal end of that lead.

In use, the channel lead can be introduced into a venous path leading to the heart through only one incision, usually made in the cephallic vein, the subsclavian vein, or the internal jugular vein. In one embodiment of the invention, the channel lead normally assumes a J-shaped configuration or an L-shaped configuration to allow convenient positioning of the distal electrode of the channel lead with tissue of the right atrial appendage or the coronary sinus. A wire stylet which maintains the distal end of the channel lead in a relatively straight configuration is withdrawn when the distal end of the channel lead is advanced to a particular location in the heart. This causes the distal end of the channel electrode to spring into its normal J-shaped or L-shaped configuration. Next, the core lead is passed through the channel lead, and exits from the channel through the side port and into the right ventricle. Usually, the vein will be tied around the channel lead to maintain it in proper position before the core lead is passed through the channel. Once the core lead is in its proper place in the right ventricle, ties are utilized to tighten the proximal end of the channel against the outer surface of core lead to prevent leakage of blood out of the heart through the channel. Sealing ridges are provided on the proximal ends of the channel lead and core lead. The distal ends of the conductors of the core lead and channel lead are plugged into recepticles of a pacemaker unit. The pacemaker unit has flexible sleeve recepticles which slide over sealing ridges of the respective proximal ends of the channel electrode and core electrode. Ties are utilized to tighten the flexible recepticles against the sealing rings to prevent leakage of blood into the pacemaker unit.

The core lead and channel lead can be either unipolar or bipolar, the unipolar leads each having two flexible conductors and two distal electrodes, and the unipolar leads having only one flexible conductor and one distal electrode.

If desired, the core lead may be positioned in the channel of the channel lead and the composite assembly may be entered as a unit through the single venous incision. If desired, a core lead can be preformed, so that it can spring into an L-shaped or J-shaped configuration when a stylet or stylets of the core lead are withdrawn; the distal end of the channel lead in this case must be initially fed into the right ventricle.

DESCRIPTION OF THE INVENTION

Figure 1A:
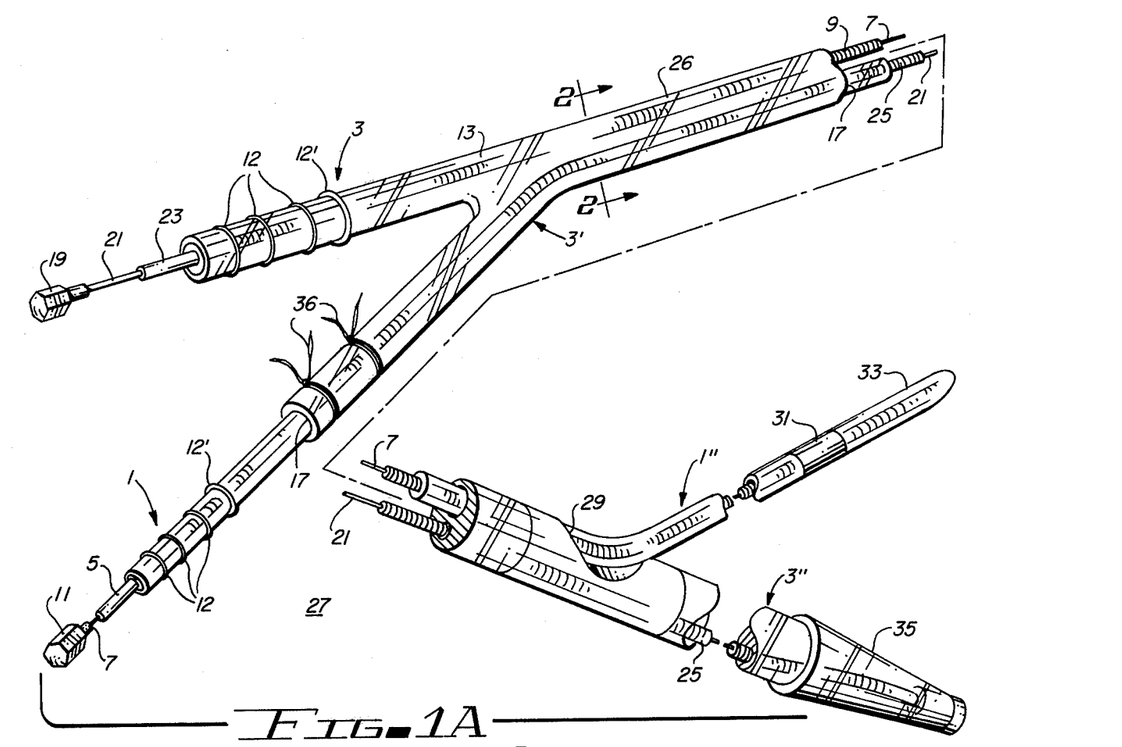
FIG. 1A is a partial perspective view of a unipolar composite lead assembly.
Figure 1B:
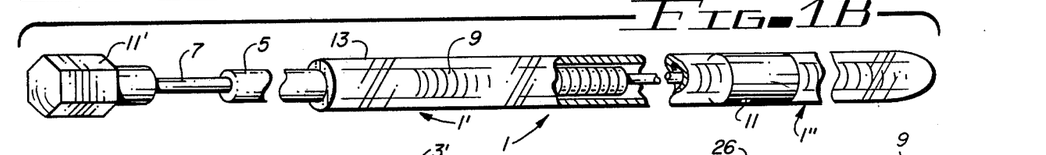
FIG. 1B is a partial perspective view of a unipolar core lead in the composite lead assembly of FIG. 1A.

Referring now to FIGS 1A-1C and FIG. 2, and particularly to FIG. 1B, core lead 1 is a typical endocardial lead including an elongated flexible silicone rubber sheath 13 through which a helical coil conductor 9 extends. Any of a variety of tips, such as ones similar to those shown in FIGS. 8-10, can be provided at the right end of tip 1" referred to as the distal end of core lead 1. Tip 1" includes electrode 11 for conducting electrical signals to or from muscle tissue electrically contacted by electrode 11 (which is referred to as a distal electrode).

At the left-hand end of core lead 1, referred to as the proximal 1', a proximal prong or electrode 5 electrically contacts helical coil conductor 9 and extends beyond silicone rubber sleeve 13. A fine spring wire stylet 7 having a predetermined bend therein extends through helical coil conductor 9 to the distal end of core lead 1. Stylet 7 has a small handle 11' attached thereto. Handle 11' can be used for rotating stylet 7 to control the distal end 1" of core lead 1 and can also be used to withdraw stylet 7 from core lead 1, whereupon proximal electrode or prong 5 can be inserted into an electrical connector of a suitable electronic device, such as a cardiac pacemaker.

Figure 1C:
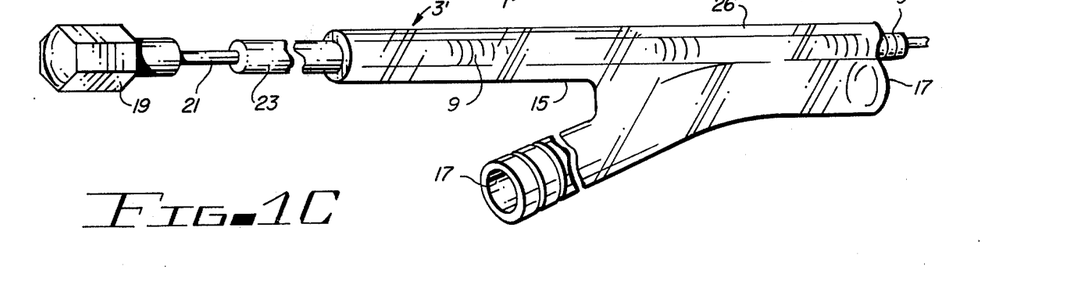
FIG. 1C is a partial perspective view of the proximal end of a unipolar channel lead of the composite lead assembly of FIG. 1A.
Figure 2:
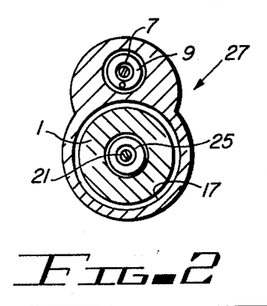
FIG. 2 discloses a sectional view along section lines 2—2 of FIG. 1A.

Referring now particularly to FIG. 1C, channel lead 3 includes a bifurcated Y-shaped proximal end structure 3' including a helical coil conductor 25 extending through one leg of the structure and through the main portion 26 of the channel lead. A second prong or electrode 23 extends from the first leg of the structure, and electrically contacts the proximal end of helical coil conductor 25. At the distal end of channel lead 3 (FIG. 1A) a suitable electrode, such as 35, is attached to the distal end of helical coil conductor 25. A hollow channel 17 extends through the second leg of channel lead 3' and continues parallel to helical coil conductor 25 through the main portion 26 of channel lead 3'. A wire stylet 21 having a handle 19 connected thereto extends through helical coil conductor 25 in the same manner that stylet 5 extends through core conductor 1.

FIG. 1A shows the proximal end 27' of a composite channel lead 27 including channel lead 3' FIG. 1C and core lead 1 of FIG. 1B inserted through channel 17 of channel lead 3'. A pair of ties 36 causes the end of leg 17 to be crimped to frictionally engage the outer surface of core lead 1, maintaining it in fixed relationship to channel lead 3', preventing body fluid from being pumped out of the heart through the space between the outer wall of core lead 1 and the inner wall of channel 17 of channel lead 3'.

FIG. 1A also shows the distal end 27" of composite unipolar channel lead 27, wherein it is seen that channel 17 of channel lead 3 terminates in a side port 29 of distal end section 27". Side port 29 includes a concave curved surface which directs core lead 1 outward from side port 29. As subsequently explained, this enables a surgeon to insert the composite unipolar channel lead 27 through a vein and facilitates positioning of the distal end of the channel lead tip 35 into either the right atrial appendage or the coronary sinus and then allows subsequent sliding of core lead 1 through channel 17 and out of side port 29, facilitating introduction of the tip 33 of core lead 1 into the right ventricle.

Figure 3:
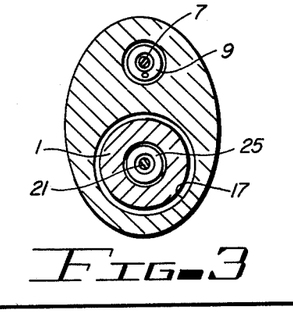
FIGS. 3 and 4 disclose alternate sectional configurations which can be used for a unipolar composite lead assembly similar to that of FIG. 1A.

FIG. 3 shows a sectional view of a slightly modified embodiment of the composite lead assembly wherein body section 26 of the channel lead 3' has an eliptical configuration.

Figure 4:
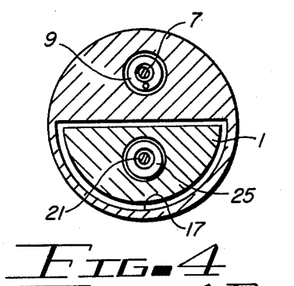

FIG. 4 discloses a sectional view of another embodiment wherein section 26 of the channel lead has a channel 17 with a semi-circular configuration and wherein the core lead 1 has a corresponding semi-circular cross-sectional configuration. The semi-circular configuration of the channel and core lead prevent any rotation of the core lead in the channel as the core lead is slid through the channel lead, which may have been previously intravenously introduced into the patient's heart.

Figure 5:
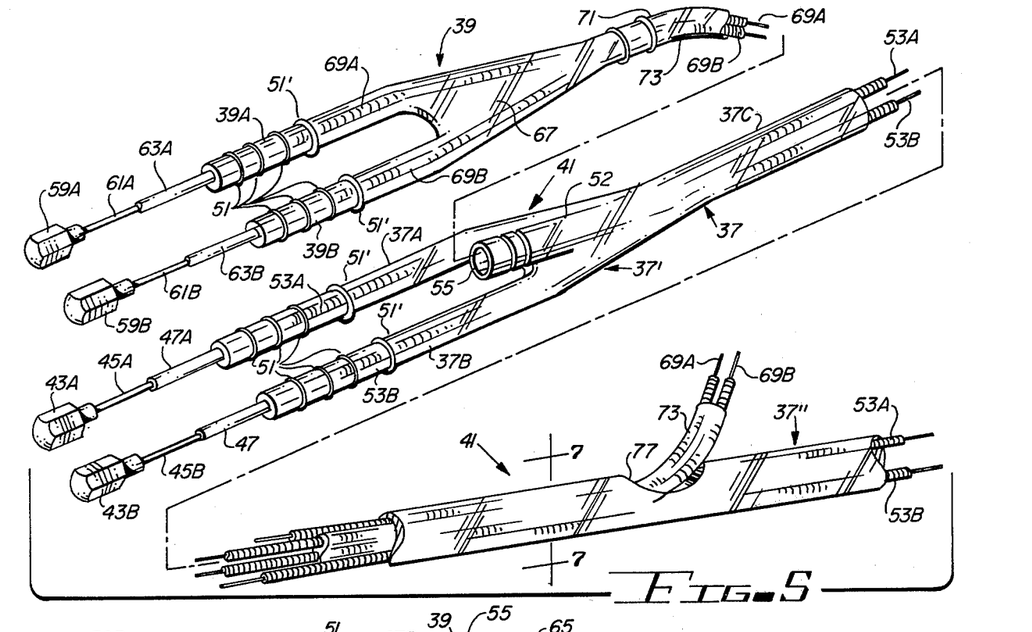
FIG. 5 is a partial exploded perspective view of a composite bipolar channel lead assembly.
Figures 6, 7, 8, 9, 10:
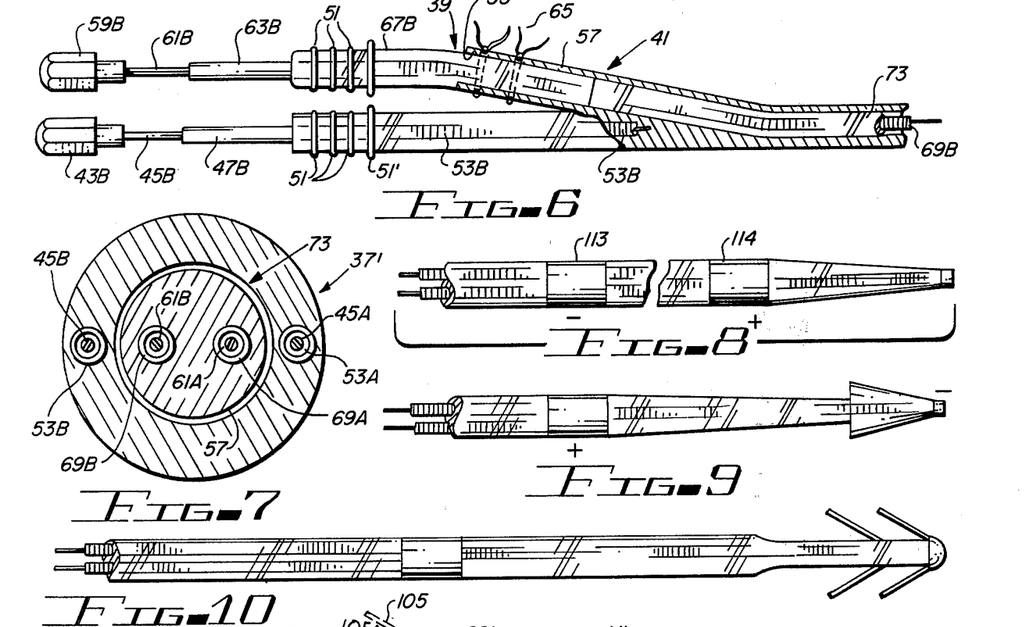
FIG. 6 is a partial cutaway side view of the proximal end of the bipolar core lead assembly of FIG. 5 with the core lead inserted in the channel lead.
FIG. 7 is a section view along section lines 7—7 of FIG. 5.
FIG. 8 is a partial side view of a bipolar electrode tip which can be used on the bipolar core or channel leads of the composite lead assembly of FIG. 5.
FIG. 9 is a side view of another bipolar electrode tip which can be used with a bipolar core lead or channel lead.
FIG. 10 is a side view of another bipolar electrode tip which can be used with a bipolar core lead or channel lead.

Referring now to FIGS. 5-7, and particularly to FIG. 5, a bipolar channel lead assembly 41 which includes bipolar channel lead 37 and bipolar core lead 39 is shown. The proximal end 1' 37' of bipolar channel lead 37 includes a silicone rubber sleeve 49 having a bifurcated end with legs 37A and 37B which join to form a unitary shaft 37C.

A channel 57, similar in purpose to channel 17 of FIG. 1B, has an enlarged entrance opening 55 disposed between legs 37A and 37B. A first helical coil conductor 53A extends through leg 37A and through unitary section 37C on one side of channel 57. A second helical coil conductor 53B extends through leg 37B and through unitary section 37C on the opposite side of channel 57.

Prongs or proximal electrodes 47A and 47B extend from the silicon rubber material of legs 37A and 37B and are electrically connected to helical coils 53A and 53B, respectively. Spring wire stylus 45A extends through prong 47A and helical conductor 53A. Stylus 45B extends in similar fashion through prong 47B and helical conductor 53B. Handles 43A and 43B are respectively connected to the proximal ends of stylets 45A and 45B.

Still referring to FIG. 5, bipolar core lead 39, which mates with bipolar channel lead 37 of FIG. 3A, also includes a pair of bifurcated leg sections 39A and 39B and a unitary section 73. Helical conductor 69A extends through leg 39A and unitary section 73. Wire stylet 61A extends through helical conductor 69A. Similarly, helical coil conductor 69B extends through leg 39B and unitary section 73. The body of bipolar core lead 39 supports and surrounds helical conductor 69A and 69B and is formed of silicone rubber. Prongs or proximal electrodes 63A and 63B are connected to the proximal ends of helical coil conductors 39A and 39B, and extend from the proximal ends of legs 39A and 39B, respectively. Handles 59A and 59B permit manipulation of stylii 61A and 61B, respectively.

Legs 39A and 39B of bipolar core lead 39 come together at a tapered section 67, which terminates at a cylindrical ridge 71. Cylindrical ridge 71 fits into enlarged channel opening 55 of FIG. 6, thereby limiting the extent to which unitary section 73 can be inserted into channel 57 of bipolar channel lead 37.

Referring now to FIG. 6, a side view of the composite bipolar channel lead assembly 41 is shown. The side view bipolar channel lead assembly 41 in FIG. 6 includes bipolar channel lead 37 with bipolar core lead 39 inserted in place, with section 73 of bipolar core lead 39 extending through channel 57 of bipolar channel lead 37.

Ties 65 compress channel opening 55 against the ridge 71 of unitary section 73, causing bipolar core lead 39 to remain in fixed relationship with bipolar channel lead 37 and prevent body fluids from being pumped through the space between the wall of channel 57 and unitary section 73 of core lead 39.

The distal end of composite bipolar channel lead assembly 41 is shown in FIG. 5, a sectional view of which is shown in FIG. 7. In FIG. 5 it is seen that channel 57 terminates in side port 77 (in the same manner that channel 17 of FIG. 1A terminates in side port 29). Concave surface 79 causes shaft 73 of bipolar core lead 39 to be directed outwardly from the axis of bipolar channel lead section 37C as unitary section 73 is forced through channel 57 and out of side port 77. This facilitates controlling the orientation of bipolar core lead 39 by a surgeon as he attempts to insert the distal end of bipolar core lead 39 into the right ventricle of the patient's heart after the core lead has first been positioned in the coronary sinus or the right atrial appendage.

Figure 11:
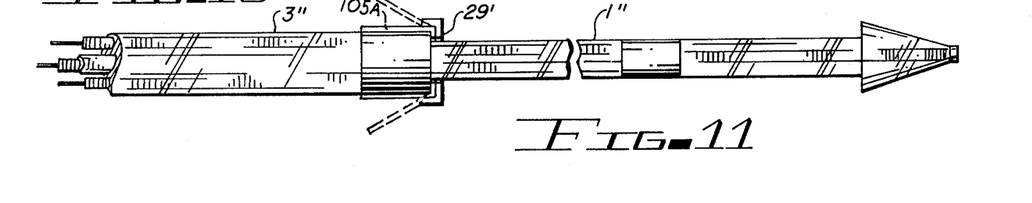
FIG. 11 is a side view of the proximal end of a composite lead assembly including a channel lead with an end port through which a core lead extends.

FIGS. 8-10 illustrate several lead tips which can be used with the above described bipolar channel lead and core lead. FIG. 8 shows a bipolar lead tip which includes spaced electrodes 113 and 114, electrode 114 being spaced from the extreme end of the bipolar tip. This bipolar lead tip can be attached to the end of any bipolar channel lead or core lead. FIG. 9 discloses a conventional bipolar lead tip with a wedge shaped electrode at its extreme end and a cylindrical electrode spaced from the wedge shaped electrode. FIG. 11 discloses another bipolar lead tip including a pair of folding tine electrodes at its extreme end and a cylindrical electrode spaced from the tine electrode. A laterally slideable cap 123 causes the tines to fold in, as indicated by 105A, or extend out, as indicated by 105. The laterally slideable cap 123 slides laterally when the enlarged electrode at the extreme right hand end of section 1" in FIG. 11 is forced out of end port 29'.

Figures 12, 13, 14:
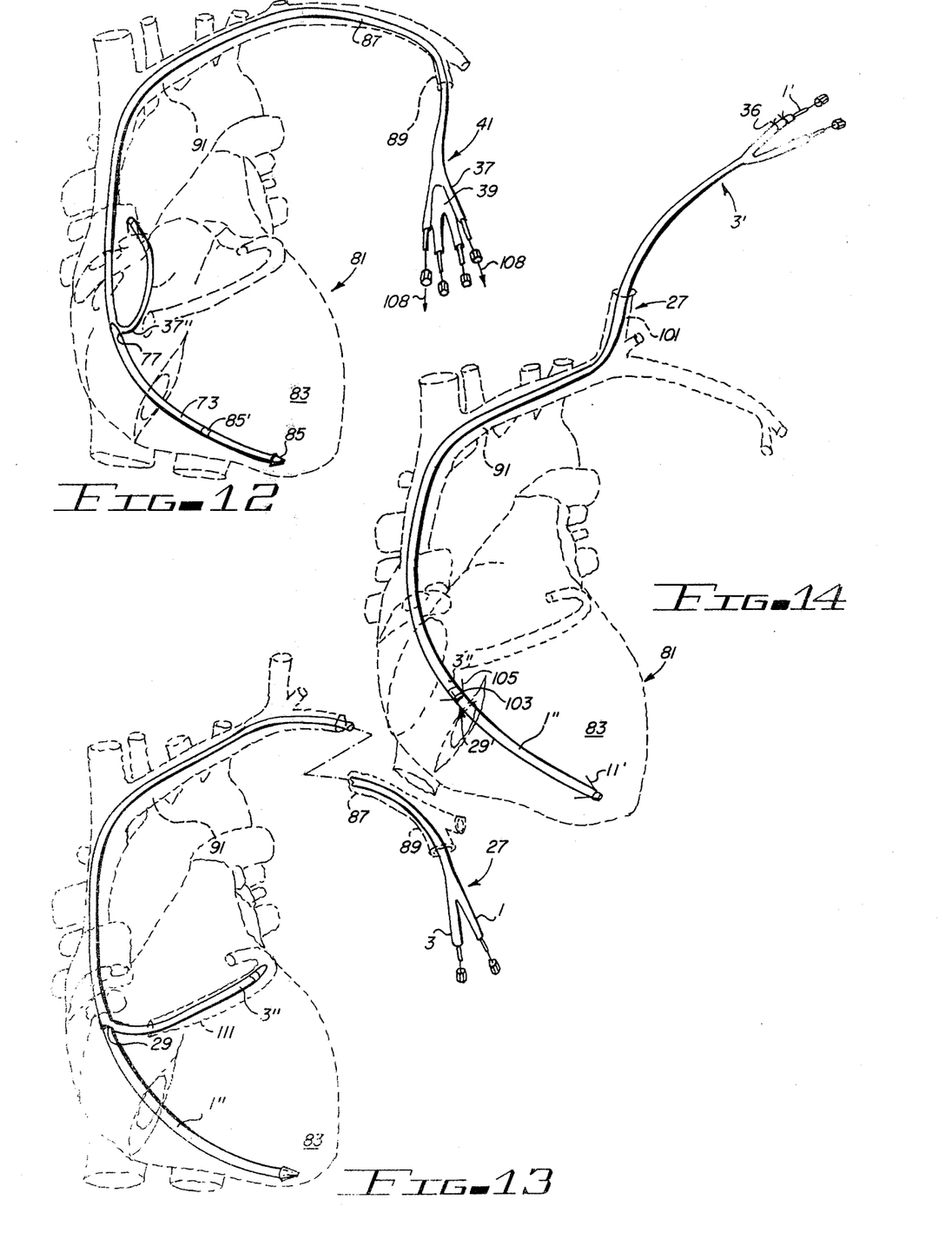
FIG. 12 shows a partial view of a human heart with the composite endocardial lead assembly of FIG. 5 positioned in the heart so that the channel lead proximal electrodes contact tissue of the right atrial appendage and the core lead distal electrodes contact tissue of the right ventricle.
FIG. 13 is a partial view of a human heart showing the composite unipolar channel lead assembly of FIG. 1A, with its core lead distal electrode contacting tissue of the right ventricle and its channel lead distal electrode contacting tissue in the coronary sinus.
FIG. 14 discloses a composite electrode wherein the channel lead has an end port with an end port electrode connected to contact the atrial tissue and a core lead extending into the right ventricle.

FIGS. 12 and 13, and 14 show several ways in which the composite leads 27 (FIG. 1) and 37 (FIG. 5) can be positioned in a patient's heart.

FIG. 12 shows the bipolar composite channel lead assembly 37 of FIG. 5 extending through the cephallic vein 89, the subclavian vein 87, and the innominate vein 91. The distal end 37" of channel lead assembly 37 springs into a J-shaped configuration as shown in FIG. 12 when stylii 45A and 45B (FIG. 5) are withdrawn. The electrodes on the end of channel lead 37 then make electrical contact with the right atrial appendage.

Section 73 of core lead 39 extends from side port 77 so that its two electrodes 85 and 85' electrically contact appropriate tissue in the right ventricle. (For convenience of illustration, the handles of stylii 45A and 45B are not shown as being withdrawn in FIG. 12, even though distal end 73" has sprung into the J-shaped configuration. Arrows 108 of FIG. 12 indicate that stylii 45A and 45B (FIG. 5) are withdrawn to allow distal end 73" to spring into the J-shaped configuration).

It should be noted that a surgeon can completely insert composite channel lead assembly 37 into the heart with the core lead 39 inserted into channel 57 but not extending out of side port 77, withdraw stylii 45A and 45B so that distal end 37" bends to contact the right atrial appendage, and then slide core lead 39 further through channel 57 so that section 73 of core lead 39 extends out of side port 77 and travels a predetermined distance into the right ventricle 83.

Alternately, the surgeon can first insert channel lead 37 alone through the cephallic, subclavian, and innominate veins, withdraw stylii 45A and 45B, causing the distal end 37" to bend to contact the right atrial appendage. Then, the surgeon can insert core lead 39 into channel 57 and slide it through channel 57 until distal end 73 of core lead 37 passes out of side port 77 and reaches the appropriate part of the right ventricle.

Next, the physician tightens "ties" 65 (FIG. 6) around flexible receptacle 55, sealing channel 57 with respect to core lead 37 to prevent blood from seeping through channel 57.

Next, the surgeon removes stylii 61A and 61B (FIG. 5) and inserts prongs 63A, 63B, 47A, and 47B into the appropriate female receptacles of a pacemaker unit or the like. The pacemaker unit has silicone rubber receptacle sleeves which slide over sealing ridges 51 and terminal sealing ridges 51' of the proximal ends of the respective leads. Ties similar to ties 65 (FIG. 6) are utilized to seal the proximal ends of channel lead 37 and core lead 39 with respect to the pacemaker unit (not shown) to prevent blood from seeping into the pacemaker electrode receptacles.

In FIG. 13, unipolar channel lead assembly 27 has been introduced into the heart through cephallic vein 89, subclavian vein 87, and innominate vein 91. Distal end 3" and its corresponding electrode extend into coronary sinus 111. Distal end 1" of core lead 1 extends out of side port 29 of channel lead 3 into ventricle 83.

The presently preferred technique is to utilize a channel lead 3 which is performed so that when wire stylet 21 is withdrawn, distal end 3" springs into an L-shaped configuration which causes distal end 3" to move into coronary sinus 111. When distal end 3" reaches the end of coronary sinus 111, core lead 1 is inserted into channel 17 of core lead 3 and passed through channel 17 until distal end 1" passes out of side port 29 and extends into the desired location of right ventricle 83. Alternately, however, composite channel electrode 27 can be introduced as a unit through the venous path shown in FIG. 13. As before, ties such as 36 (FIG. 1A) must be applied to prevent leakage of blood after the electrodes of distal end 3" of core lead 3 and 1" of core lead 1 are properly lodged in the coronary sinus and right ventricle, respectively.

FIG. 14 discloses unipolar channel lead assembly 27 inserted through internal jugular vein 1, innominate vein 91 through the atrium and into right ventricle 83. The embodiment of bipolar channel lead assembly 27 shown in FIG. 14 has an end port 29. (FIG. 11 shows in detail the structure of the distal electrodes of FIG. 14, wherein electrode tines 105 are attached to the extreme end of channel lead 5. When the above mentioned laterally slideable cap shown in FIG. 11 slides forward, the folded tines indicated by reference numeral 105A spring outward as indicated by reference numeral 105. The channel of channel lead 5 terminates in an end port 29' located at the extreme distal end 3" of channel lead 3. The distal end 1" of core lead 1 extends out of end port 29'). Electrode 103 of distal end 3" of channel lead 3 has a pair of tines 105 which are actuated by forward movement of the above mentioned laterally slideable cap 123 to hook into the atrial tissue. Distal end 1" of core lead 1 has electrode 11', which engages muscle tissue in the right ventricle 83. Ties 36 seal the channel of channel lead 3 with respect to core lead 1. Again, composite channel lead assembly 27 can be fed into heart 81 as a single unit, or channel lead 3 first can be introduced into the heart alone, and then core lead 1 can be slid through channel 17 of channel lead 3, so that the distal end 1" of core lead 1 passes through end port 29' until it reaches its final destination in ventricle 83.

It should be noted, however, that although the lead placements shown in FIGS. 12 and 13 are presently preferred, it is also possible to reverse the roles of the distal ends of the channel and core leads, so that the core "springs" into the J-shaped configuration necessary to contact the right atrial appendage or pass into the coronary sinus when the core lead stylet or stylii are withdrawn, after which time the distal end of the channel lead is passed into the right ventricle. The latter approach, however, may cause some difficulty, since more skillful manipulation is required to place leads in the right atrial appendage or the coronary sinus. It is believed to be best to position and lodge a lead in the atrial appendage or coronary sinus first since it is usually a relatively simple matter to position and lodge a lead in the right ventricle.

Figure 15:
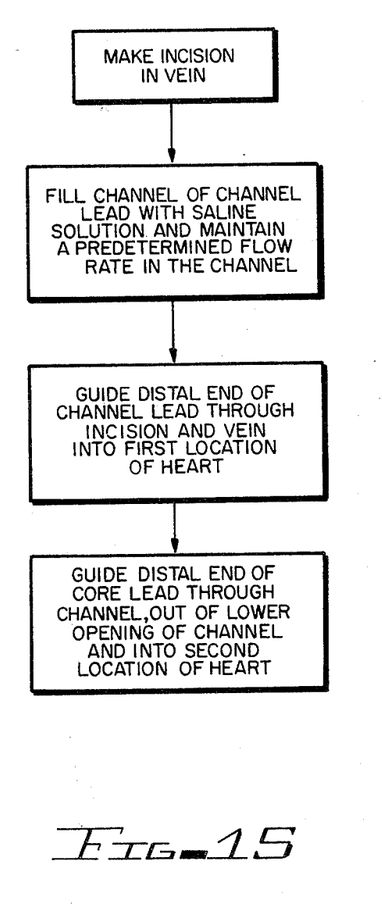
FIG. 15 is a flow chart useful in explaining one embodiment of the invention.

As previously mentioned, intravenous insertion of a channel lead into a patient's heart can be accomplished with the core lead positioned in the channel at the time of introduction of the channel lead and through an appropriate venous entry site. Alternatively, if passage of the core lead tip is compatable with the diameter of the channel such that the core lead tip can be passed through the channel after the channel lead has been positioned in the patient's heart, then the channel lead may be introduced into an appropriate venous incision, through an intravenous pathway to the heart, and into the appropriate heart chamber without the core lead being positioned in the channel of the channel lead. If the latter method is employed, the open channel of the channel lead first can be filled with a sterile intravenous solution, such as normal saline solution. The proximal channel opening can then be connected to a pump that produces a controlled rate of intravenous infusion of normal saline solution, so that no blood will flow into the channel (possibly producing clots or blood loss) during passage of the open-channel channel lead into the venous entry site. The flow chart of FIG. 15 illustrates the foregoing procedure. Alternatively, after the channel is filled with a sterile solution (such as the above mentioned normal saline solution), the proximal end of the channel can be capped during introduction of the open-channel channel lead into the selected venous entry site.

While the invention has been described with reference to several embodiments thereof, those skilled in the art will be able to make variations in the disclosed structure and method which are well within the purview of those skilled in the art without departing from the true spirit and scope of the present invention. For example, a plurality of silicone rubber straps or clips integrally formed with one lead could slideably engage a second lead against the first lead. This approach would work in situations wherein it is acceptible to introduce a composite lead through a venous path into the heart. However, this approach would not work if it were desirable to first introduce one lead into the heart, since it would be imposssible to pass the free end of a second lead through the silicone rubber straps or clips.

I claim:

1. A lead assembly for intravenously conducting electrical signals to or from a patient's heart, the lead assembly comprising in combination:
   a. a core lead having first and second ends, said core lead including
      i. first flexible sleeve means;
      ii. a first conductor surrounded by material of said first flexible sleeve means, said first conductor extending approximately between the first and second ends of said core lead;
      iii. first electrode means attached to said first flexible sleeve means approximately at the first end of said core lead, said first electrode means being electrically connected to said first conductor;
   b. a first removable stylet extending through said first flexible sleeve means to facilitate control of said core lead, said core lead being preformed to tend to assume a straight configuration when said first stylet is removed from said core lead;
   c. a channel lead having first and second ends, said channel lead including
      i. second flexible sleeve means, said second flexible sleeve means having an elongated channel for receiving said core lead, said channel extending through a major portion of the length of said channel lead, said channel extending from a first opening in said channel lead to a second opening in said channel lead, said first opening being located at said first end of said channel lead, said second opening being a side port opening located a first predetermined distance from said second end of said channel lead;
      ii. a second conductor surrounded by material of said second flexible sleeve means, said second conductor being disposed outside of said channel and extending approximately between the first and second ends of said second flexible sleeve means;
      iii. second electrode means attached to said second flexible sleeve means approximately at the first end of said channel lead, said second electrode means being electrically connected to said second conductor; and
   d. a second removable stylet extending through said second flexible sleeve means to facilitate control of said channel lead, said core lead being disposed in said channel of said channel lead, the first end of said core lead extending from said first opening and the second end of said core lead extending from said second opening, said first opening being located within the patient's heart when said channel lead is positioned to conduct the electrical signals to a predetermined portion of the patient's heart, said channel lead being performed to tend to assume a bent, J-shaped configuration located approximately at the location of said side port opening to cause said second end of said channel lead to move into the atrial appendage of the patient's heart when said second stylet is removed, said side port opening being located near the lowest portion of said bent, J-shaped configuration when the second end of said channel lead is in the highest or superior portion of the atrial appendage, said core lead extending through said side port opening deep into the right ventricle of the patient's heart.

2. The lead assembly of claim 1 wherein said first and second flexible sleeve means are composed of silicone rubber.

3. The lead assembly of claim 2 wherein said first conductor means is a helically wound coil conductor.

4. The lead assembly of claim 2 wherein said core lead and said channel lead each include a circumferential sealing ring of silicone rubber extending from said first and second flexible sleeve means adjacent the second ends of said core lead and said channel lead, respectively, for sealing said core lead and said channel lead to receptacles of an electronic signal producing and/or receiving apparatus.

5. The lead assembly of claim 2 wherein the second end of said channel lead is divided into first and second branches, said channel extending through the first branch, said lead assembly including ties for tightening silicone rubber material of said first branch against said core lead to form a seal between the silicone rubber material of said first branch and the silicone rubber material of said core lead to prevent blood from seeping from the patient's heart through said channel.

6. The lead assembly of claim 2 wherein said core lead and said channel lead are both bipolar leads.

7. The lead assembly of claim 1 wherein said core lead further includes third electrode means electrically connected to said first conductor at the second end of said core lead for electrically connecting said core lead to an electronic signal sending and/or receiving apparatus, and wherein said channel lead further includes fourth electrode means electrically connected to said second conductor at the second end of said channel lead.

8. A lead assembly for intravenously conducting electrical signals to or from a patient's heart, the lead assembly comprising in combination:
   a. a core lead having first and second ends, said core lead including
      i. first flexible sleeve means;
      ii. a first conductor surrounded by material of said first flexible sleeve means, said first conductor extending approximately between the first and second ends of said core lead;
      iii. first electrode means attached to said first flexible sleeve means approximately at the first end of said core lead, said first electrode means being electrically connected to said first conductor;
   b. a first removable stylet extending through said first flexible sleeve means to facilitate control of said core lead, said core lead being preformed to tend to assume a straight configuration when said first stylet is removed from said core lead;
   c. a channel lead having first and second ends, said channel lead including
      i. second flexible sleeve means, said second flexible sleeve means having an elongated channel for receiving said core lead, said channel extending through a major portion of the length of said channel lead, said channel extending from a first opening in said channel lead, said first opening being located at said first end of said channel lead, said second opening being a side port opening located a first predetermined distance from said second end of said channel lead;
      iii. a second conductor surrounded by material of said second flexible sleeve means, said second conductor being disposed outside of said channel and extending approximately between the first and second ends of said second flexible sleeve means;
      iii. second electrode means attached to said second flexible sleeve means approximately at the first end of said channel lead, said second electrode means being electrically connected to said second conductor; and
   d. a second removable stylet extending through said second flexible sleeve means to facilitate control of said channel lead, said core lead being disposed in said channel of said channel lead, the first end of said core lead extending from said first opening and the second end of said core lead extending from said second opening, said first opening being located within the patient's heart when said channel lead is positioned to conduct the electrical signals to a predetermined portion of the patient's heart, said channel lead being preformed to tend to assume a bent, L-shaped configuration located approximately at the location of said side port opening to cause said second end of said channel lead to move into the coronary sinus of the patient's heart when said second stylet is removed, said side port opening being located near the entrance to the coronary sinus when the second end of said channel lead is in the deepest portion of the coronary sinus, said core lead extending through said side port opening deep into the right ventricle of the patient's heart.

9. A method for intravenously introducing first and second leads into a patient's heart, said method comprising the steps of:
   a. making only one incision in only one vein in a venous path leading to the patient's heart;
   b. inserting a first end of a channel lead into the vein through the incision, the channel lead having a first end and a second end, the channel lead having an elongated channel terminating in a side port opening located a predetermined distance from the second end of the channel lead, the channel being capable of accommodating passing of a core lead through the channel, the core lead having a first end and a second end;
   c. guiding the first end of the channel lead through a venous path to the entrance of the atrial appendage of the patient's heart;
   d. withdrawing a stylet from the channel lead, the channel lead being preformed to assume a J-shaped configuration with a bend located approximately at the location of said side port opening when the stylet is withdrawn to direct the first end of the core lead into the atrial appendage of the patient's heart, said channel lead being preformed to tend to assume a J-shaped configuration to cause the second end of said channel lead to move into the atrial appendage of the patient's heart when the stylet is removed, said side port opening being located near the lowest portion of said bend when the second end of said channel lead is in the highest or superior portion of the atrial appendage;
   e. guiding the first end of said channel lead deep into the atrial appendage; and f. guiding the first end of said core lead through the channel, out of said side port opening, into the right ventricle of the patient's heart.

10. The method of claim 9 further including the step of sealing the channel of the channel lead to the core lead to prevent sliding of the core lead in the channel and to prevent leakage of blood from the heart through the channel.

11. The method of claim 9 including the step of sealing the channel lead to the vein prior to step (e) to prevent sliding of the channel lead in the vein and to prevent loss of blood from the heart through the incision.

12. A method for intravenously introducing first and second leads into a patient's heart, said method comprising the steps of:
   a. making only one incision in only one vein in a venous path leading to the patient's heart;
   b. inserting a first end of a channel lead into the vein through the incision, the channel lead having a first end and a second end, the channel lead having an elongated channel terminating in side port opening located a predetermined distance from the first end of the channel lead, the channel being capable of accommodating passing of a core lead through the channel, the core lead having a first end and a second end;
   c. guiding the first end of the channel lead through a venous path to the entrance of the coronary sinus of the patient's heart;
   d. withdrawing a stylet from the channel lead, the channel lead being preformed to assume an L-shaped configuration with a bend located approximately at the location of said side port opening when the stylet is withdrawn to direct the first end of the core lead into the coronary sinus of the patient's heart, said channel lead being preformed to tend to assume an L-shaped configuration to cause the second end of said channel lead to move into the coronary sinus of the patient's heart when the stylet is removed, said side port opening being located near the entrance to the coronary sinus when the second end of said channel lead is in the deepest portion of the coronary sinus;
   e. guiding the first end of said channel lead deep into the coronary sinus; and
   f. guiding the first end of the core lead through the channel, out of the side port opening, into the right ventricle of the patient's heart.

13. A method for intravenously introducing first and second leads into a patient's heart, said method comprising the steps of:
   a. making a single incision into only one vein in a venous path leading to the patient's heart;
   b. inserting a first end of a channel lead into the vein through the incision, the channel lead having a first end and a first opening at the first end and a second end and a second opening located a predetermined distance from the second end, the channel lead having an elongated channel extending between the first and second openings of the channel lead, the channel being capable of accommodating passing of a first end of a core lead through the channel and out of the second opening of the channel, said method including filing the channel with a sterile intravenous solution and connecting the first opening of the channel lead to a device that produces a controlled flow of said sterile intravenous solution into the channel before said inserting of the first end of the channel lead into the vein through the incision;
   c. guiding the first end of the channel lead through the venous path to a first predetermined location in the patient's heart; and
   d. inserting the first end of the core lead into the first opening of the channel lead and forcing the first end of the core lead through the channel and out of the second opening of the channel lead and guiding the first end of the core lead to a second predetermined location in the patient's heart while maintaining the first end of the channel lead substantially at said first predetermined location.

14. The method of claim 13 wherein said sterile intravenous solution is normal saline solution.

15. A method for intravenously introducing first and second leads into a patient's heart, said method comprising the steps of:
   a. making only one incision in only one vein in a venous path leading to the patient's heart;
   b. inserting a first end of a channel lead into the vein through the incision, the channel lead having a first end and a second end, the channel lead having an elongated channel terminating in a side port opening located a predetermined distance from the second end of the channel lead, the channel being capable of accommodating passing of a core lead through the channel, the core lead having a first end and a second end;
   c. guiding the first end of the channel lead through a venous path to the entrance of a first predetermined cavity of the patient's heart;
   d. withdrawing a stylet from the channel lead, the channel lead being preformed to assume a bent configuration with a bend located approximately at the location of said side port opening when the stylet is withdrawn in order to direct the first end of the core lead into said predetermined cavity in the patient's heart adjacent to said venous path, said channel lead being preformed to tend to assume said bent configuration to cause the second end of said channel lead to move into said predetermined cavity of the patient's heart when the stylet is removed, said side port opening being located near the lowest portion of said bend when the second end of said channel lead is in the deepest portion of said predetermined cavity;
   e. guiding the first end of said channel lead deep into said predetermined cavity; and
   f. guiding the first end of said core lead through the channel, out of said side port opening, into the right ventrical of the patient's heart.

16. A lead assembly for intravenously conducting electrical signals through a venous path to or from a patient's heart, the lead assembly comprising in combination:
   a. a core lead having first and second ends, said core lead including
      i. first flexible sleeve means;
      ii. a first conductor surrounded by material of said first flexible sleeve means, said first conductor extending approximately between the first and second ends of said core lead;
      iii. first electrode means attached to said first flexible sleeve means approximately at the first end of said core lead, said first electrode means being electrically connected to said first conductor;

b. a first removable stylet extending through said first flexible sleeve means to facilitate control of said core lead, said core lead being preformed to tend to assume a straight configuration when said first stylet is removed from said core leads;

c. a channel lead having first and second ends, said channel lead including i. second flexible sleeve means, said second flexible sleeve means having an elongated channel for receiving said core lead, said channel extending through a major portion of the length of said channel lead, said channel extending from a first opening in said channel lead to a second opening in said channel lead, said first opening being located at said first end of said channel lead, said second opening being a side port opening located a first predetermined distance from said second end of said channel lead;

ii. a second conductor surrounded by material of said second flexible sleeve means, said second conductor being disposed outside of said channel and extending approximately between the first and second ends of said second flexible sleeve means;

iii. second electrode means attached to said second flexible sleeve means approximately at the first end of said channel lead, said second electrode means being electrically connected to said second conductor; and d. a second removable stylet extending through said second flexible sleeve means to facilitate control of said channel lead, said core lead being disposed in said channel lead, the first end of said core lead extending from said first opening and the second end of said core lead extending from said second opening, said first opening being located within the patient's heart when said channel lead is positioned to conduct the electrical signals to a predetermined portion of the patient's heart, said channel lead being preformed to tend to assume a bent configuration located approximately at the location of said side port opening to cause said second end of said channel lead to move into a predetermined cavity in the patient's heart adjacent to said venous path when said second stylet is removed, said side port opening being located near the entrance to said predetermined cavity when the second end of said channel lead is in the deepest portion of said predetermined cavity, said core lead extending slidably through said side port opening deep into the right ventricle of the patient's heart.

* * * * *